United States Patent
Bennison

(10) Patent No.: US 8,197,431 B2
(45) Date of Patent: Jun. 12, 2012

(54) ACOUSTIC ACCESS DISCONNECT DETECTION SYSTEM

(75) Inventor: Corrie Bennison, Lewis Center, OH (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 622 days.

(21) Appl. No.: 11/859,561

(22) Filed: Sep. 21, 2007

(65) Prior Publication Data

US 2009/0082676 A1  Mar. 26, 2009

(51) Int. Cl.
*A61M 37/00* (2006.01)
*A61B 8/14* (2006.01)

(52) U.S. Cl. .................... 604/6.06; 600/462

(58) Field of Classification Search .......... 600/485–490; 604/4.01–6.16, 8–10, 65–67, 27–31; 210/644–650; 422/44–48
See application file for complete search history.

(56) References Cited

U.S. PATENT DOCUMENTS

| | | | |
|---|---|---|---|
| 3,882,861 A | 5/1975 | Kettering et al. | |
| 3,946,731 A | 3/1976 | Lichtenstein | |
| 4,450,527 A | 5/1984 | Sramek | |
| 4,501,583 A | 2/1985 | Troutner | |
| 4,534,756 A | 8/1985 | Nelson | |
| 4,648,869 A | 3/1987 | Bobo, Jr. | |
| 4,710,163 A | 12/1987 | Butterfield | |
| 4,770,787 A * | 9/1988 | Heath et al. ............. | 210/646 |
| 4,846,792 A | 7/1989 | Bobo, Jr. | |
| 4,979,940 A | 12/1990 | Bobo, Jr. | |
| 4,981,467 A | 1/1991 | Bobo, Jr. et al. | |
| 5,026,348 A | 6/1991 | Venegas | |
| 5,100,374 A | 3/1992 | Kageyama | |
| 5,146,414 A | 9/1992 | McKown et al. | |
| 5,427,695 A | 6/1995 | Brown | |
| 5,473,214 A | 12/1995 | Hildebrand | |
| 5,557,263 A | 9/1996 | Fisher et al. | |
| 5,723,775 A | 3/1998 | Watanabe et al. | |
| 5,790,036 A | 8/1998 | Fisher et al. | |
| 5,863,421 A | 1/1999 | Peter, Jr. et al. | |
| 6,071,421 A | 6/2000 | Brown | |
| 6,077,443 A | 6/2000 | Goldau | |
| 6,090,048 A * | 7/2000 | Hertz et al. ............. | 600/485 |
| 6,167,765 B1 | 1/2001 | Weitzel | |

(Continued)

FOREIGN PATENT DOCUMENTS

EP  0293592 A2  12/1988

(Continued)

*Primary Examiner* — Tatyana Zalukaeva
*Assistant Examiner* — Philip R Wiest
(74) *Attorney, Agent, or Firm* — K&L Gates LLP

(57) ABSTRACT

An acoustic access disconnect detection system is useful for detecting when an access needle has become dislodged or when blood is leaking. The acoustic disconnect detection system includes an acoustic transmitter and one or more acoustic sensors placed upstream of an access site of a patient, the sensors suitable for generating and detecting an acoustic signal that is intended to pass unobstructed through the access site. The acoustic transmitter may be placed on a therapy machine for generating an acoustic signal. The acoustic sensor is mounted downstream of the transmitter, such as on the therapy machine where blood is pumped to or returned from the patient, on the patient, or on the therapy machine where blood is entering the therapy machine. The therapy machine, such as a dialysis machine, may be programmed not to start or continue operation unless the acoustic signal is within certain parameters.

17 Claims, 9 Drawing Sheets

U.S. PATENT DOCUMENTS

| | | |
|---|---|---|
| 6,187,199 B1 | 2/2001 | Goldau |
| 6,221,040 B1 | 4/2001 | Kleinekofort |
| 6,572,576 B2 | 6/2003 | Brugger et al. |
| 6,575,927 B1 | 6/2003 | Weitzel et al. |
| 6,595,942 B2 | 7/2003 | Kleinekofort |
| 6,623,443 B1 | 9/2003 | Polaschegg |
| 6,736,789 B1 | 5/2004 | Spickermann |
| 6,767,333 B1 | 7/2004 | Müller et al. |
| 6,780,159 B2 | 8/2004 | Sandler et al. |
| 6,804,991 B2 | 10/2004 | Balschat et al. |
| 6,827,698 B1 | 12/2004 | Kleinekofort |
| 6,880,404 B2 | 4/2005 | Überreiter |
| 7,040,142 B2 | 5/2006 | Burbank |
| 7,172,569 B2 | 2/2007 | Kleinekofort |
| 7,172,570 B2 | 2/2007 | Cavalcanti et al. |
| 7,204,958 B2 * | 4/2007 | Olsen et al. .................. 422/44 |
| 2004/0171977 A1 | 9/2004 | Paolini et al. |
| 2005/0010118 A1 | 1/2005 | Toyoda et al. |
| 2008/0065006 A1 | 3/2008 | Roger |
| 2008/0195021 A1 * | 8/2008 | Roger et al. ................ 604/4.01 |
| 2008/0195060 A1 | 8/2008 | Roger |
| 2009/0079578 A1 | 3/2009 | Dvorsky |
| 2009/0080757 A1 | 3/2009 | Roger |
| 2009/0082646 A1 | 3/2009 | Bouton |
| 2009/0082647 A1 | 3/2009 | Busby |
| 2009/0082649 A1 | 3/2009 | Muller |
| 2009/0082653 A1 | 3/2009 | Rohde |
| 2009/0088612 A1 | 4/2009 | Bouton |
| 2009/0088613 A1 | 4/2009 | Marttila |
| 2009/0088683 A1 | 4/2009 | Roger |
| 2009/0105627 A1 | 4/2009 | Rohde |
| 2010/0022934 A1 | 1/2010 | Hogard |
| 2010/0022935 A1 | 1/2010 | Muller |

FOREIGN PATENT DOCUMENTS

| | | |
|---|---|---|
| WO | 97/10013 A1 | 3/1997 |
| WO | WO03/002174 | 1/2003 |
| WO | 2008/100671 A1 | 8/2008 |
| WO | PCT/US2008/066051 | 11/2008 |

* cited by examiner

ACOUSTIC ACCESS DISCONNECT DETECTION SYSTEM

BACKGROUND

The field of the invention is medical treatments generally and patient vascular access systems. The present invention relates to embodiments of a method and a system for detecting disconnection of an access needle or catheter while receiving medical treatment.

The maxim of "first, do no harm," may be a good summary of the Hippocratic oath required of doctors and practiced by medical professionals. Nowhere is this principle required more than in modem medicine. With patients living longer, there are more extended treatments and more frail patients than ever. Such patients are in danger from a number of complications that can arise from continuing therapeutic procedures, and even from diagnostic procedures, that are necessary for their continued care. Treatments involving extracorporeal blood treatment are clear examples.

The most obvious danger is infection, but the harm caused by infection can be overcome by not re-using even supposedly-sterile devices, by diligent attention by the patient himself or herself, and by the careful attention of care givers attending the patient. Other problems also arise, but, like infections, have been difficult to eradicate. One of the problems arises in blood treatment procedures in which the patient's blood is physically removed for treatment and then returned, all in the same procedure. Removal and return of blood is practiced in hemodialysis, for those persons whose kidneys do not function well. Other procedures, such as apheresis, involve removing blood from a patient or a donor to separate blood platelets or plasma from the red blood cells, and then returning the red blood cells to the patient or donor, as described in U.S. Pat. Nos. 5,427,695 and 6,071,421.

The extracorporeal medical treatments described above require that the blood be removed for treatment and then returned. This requires access to the patient's vascular system, from which blood is removed and to which blood is then returned. If a "batch" treatment is used, that is, a quantity of blood is withdrawn, treated and returned, only a single needle is used. Each batch treatment is typically short, and the treatment is attended by a medical professional at a clinic or hospital. Other treatments are continuous, such as the platelet separation discussed above, or dialysis treatment, and may require a duration of several hours or even overnight. Yet other treatments use a "batch" continuous method in which only a single needle is used. There are distinct withdraw and return phases in a batch continuous process. During the draw phase, blood is processed and additional blood is sent to a holding container to be processed during the return phase. In the return phase, blood is processed from the holding container and then returned to the patient or donor through the single needle.

Continuous treatments require two needles, or access points, one for withdrawal of blood and one for return. The withdrawal site is normally an artery, and a needle and a pump are used to provide the blood to the therapeutic machine, but in some treatments, such as apheresis, blood is withdrawn from and returned to veins. It is relatively simple to detect a problem with withdrawal, for instance, if the withdrawal needle is dislodged, using conventional air sensor technology. Detecting a problem in the return of the blood to the patient is more difficult. The return line typically includes a needle with venous access. If the return line is dislodged, the blood is not returned to the patient, but may continue to be pumped and may accumulate near the patient, but not returned to the patient's vascular system. Depending on the pumping rate of the blood and the time for treatment, this could have life-threatening effects on the patient within a very short period time.

Accordingly, a number of apparatuses have been devised for detecting needle dislodgement, especially venous dislodgement. Many of these techniques use pressure monitoring of the venous access line. One example is U.S. Pat. No. 6,077,443. This patent uses a pressure sensor mounted near a drip chamber to monitor pressure pulses from a blood pump. There appears to be very little difference between the signals when the access needle is properly in place and the signals when the access needle has been removed. In another example, U.S. Pat. No. 6,221,040, pressure-sensing equipment is made more sensitive, but this case results in a higher rate of false positives, i.e., false alarms.

Another method is disclosed in U.S. Pat. No. 6,572,576. This patent discloses periodically generating a negative pressure in the return line. This causes air to be drawn into the line, which can then be detected by a standard air sensor. This also has some negative aspects, since no air can be allowed in blood returned to the patient. Any mishandling in this area, such as that resulting from worn tubing, could result in blood in the air line with disastrous consequences. What is needed is an access disconnect device that overcomes these difficulties while providing a safe and quick indication to the patient or caregiver that a disconnect or a leak has occurred.

SUMMARY

One embodiment is an access disconnect detector. The access disconnect detector includes an acoustic transmitter for producing an acoustic signal and configured for mounting upstream of a venous access site, an acoustic sensor for sensing a signal from the acoustic transmitter, the acoustic sensor mounted downstream from the transmitter, and a controller configured for sensing signals from the acoustic transmitter and the acoustic sensor and for sending an alert upon a change in the signals detected from the acoustic transmitter or the acoustic sensor, wherein the controller is in communication with or is part of a therapy machine for receiving blood and returning blood to the venous access site.

Another embodiment is an acoustic access disconnect detector. The acoustic access disconnect detector includes an acoustic transmitter for producing an acoustic signal and configured for mounting on a therapy machine, at least one acoustic sensor for sensing a signal from the acoustic transmitter, and a controller configured for sensing signals from the acoustic transmitter and the acoustic sensor and for sending an alert upon a change in the signals from the acoustic transmitter or the acoustic sensor, wherein the controller is in communication with or is part of a therapy machine for receiving blood and returning blood to a patient.

Another embodiment is a method for detecting an access disconnection. The method includes steps of sending an acoustic signal into a venous access device, detecting the acoustic signal downstream of a point of origin of the acoustic signal, comparing the detected acoustic signal with baseline detected acoustic signals, deciding whether the detected acoustic signal is significantly different from the baseline detected acoustic signals, and sending an alert if the detected acoustic signal is significantly different from the baseline acoustic signals.

Another embodiment is a method for detecting an access disconnect. The method includes steps of placing an acoustic sensor upstream of a venous access site, detecting a first heart beat of a patient, determining a first baseline signal from the first heart beat, sensing a second heart beat of the patient, determining a second baseline signal from the second heart beat, comparing the second baseline signal to the first baseline signal, and sending an alert if the step of comparing indicates that the access disconnect or a leak has occurred.

Additional features and advantages are described herein, and will be apparent from, the following Detailed Description and the figures.

DETAILED DESCRIPTION

It is important that venous disconnects should be detected quickly and therapy stopped without delay when a disconnect occurs. As noted above, sending acoustic signals from the therapy machine and insuring that the signals arrive at the venous access site in sufficient magnitude is one way to insure patient safety. The goal of an access disconnect detector is to insure that the needle or other access device is continuously and firmly lodged in its correct location. Acoustics provide a unique, non-invasive way to accomplish this. Once it is decided to use this method, attention then focuses on the location of the transducer or other device to generate an acoustic signal, and also on the location of the sensor or other device to receive the signal.

The theory is that if access disconnect occurs, the signals will not continue into the access site and there will be a break in the transmission, greater reflection of the signals, and other acoustic events. In any event there should be a significant change in the signal detected by the acoustic sensor. There will also be a significant change in the phases, i.e., in the timing of the acoustic signals as the sensor sees them.

This patent will discuss several ways to use acoustics to detect access disconnects and leaks in the venous access site, both of which, in theory, should cause a change in the acoustic transmission medium, and therefore a change in the signal received. The methods discussed will include acoustic generation and reception ("pitch and catch"), also known as the acoustic signature method. Another method is to calculate a reflection coefficient of the media, which uses a ratio of the reflected and incident waves to more readily detect a discontinuity or change. Another method is acoustic impedance, which is based on the fact that when the transmission medium is disturbed, there will be a difference in the impedance of a first medium and a second medium, such as air and water. Finally, it is also possible to use the patient's own heart beat to detect a discontinuity in the venous or arterial access site.

Acoustic Signature

Figure 1:
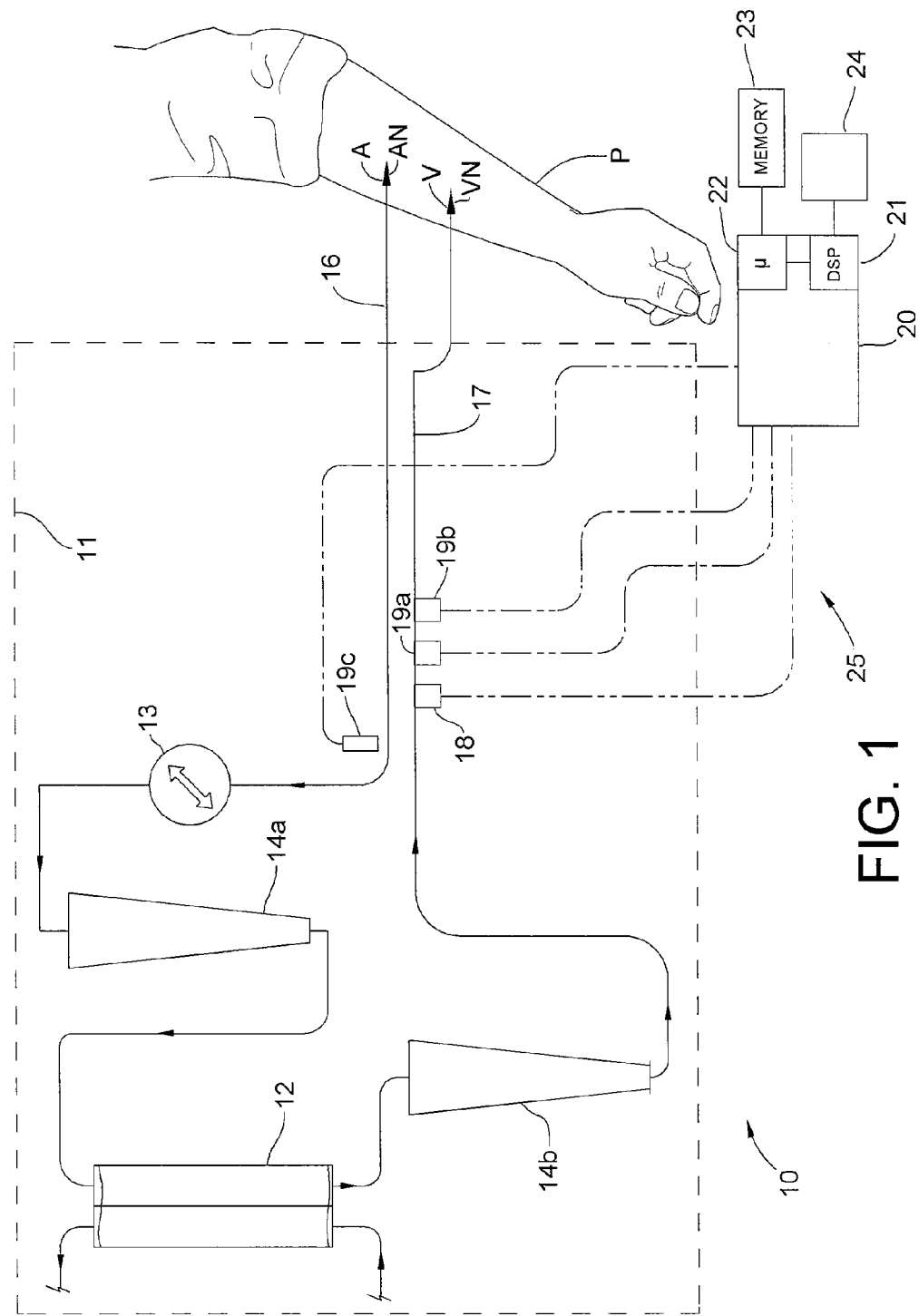
FIG. 1 depicts a schematic view of an embodiment of a hemodialysis machine using acoustics to detect a venous disconnect.

In FIG. 1, a patient P is connected to a therapy machine, such as hemodialysis machine 10, and cassette 11, via an arterial access A and a venous access V. The therapy machine includes a renal failure therapy fluid pumping cassette 11, a twin-chamber dialyzer 12, one or more blood pumps 13, and arterial and venous drip chambers 14a, 14b. Arterial access A is connected to the hemodialysis machine 10 via inlet tubing 16 and arterial access needle $A_n$, and venous access V is connected to the hemodialysis machine via outlet tubing 17 and venous access needle $V_n$. An acoustic transmitter 18, used to induce or transmit an acoustic signal, is mounted on the hemodialysis machine, and on the cassette in particular, and an acoustic sensor 19a is mounted adjacent acoustic transmitter 18. A second acoustic sensor 19b may also be mounted adjacent acoustic sensor 19a. An additional acoustic sensor 19c may also be mounted on the arterial input portion of the cassette 11. As shown below, the acoustic sensors are mounted inside the hemodialysis machine to interface with the cassette.

Acoustic transducer 18 is configured for generating and sending an acoustic signal into tubing 17 so that the signal is transmitted through the tubing, into venous access needle $V_n$ and into the patient P. Acoustic sensor 19a is mounted adjacent the acoustic transmitter for detecting the signal sent by transducer 18 and also signals returned from the downstream tubing and connections. It is clear that the signal generated by transducer 18 will be attenuated by its path through tubing 17, venous access needle $V_n$, and the patient. Thus, the signal received by sensor 19a will likely be much diminished in magnitude, and there is also a time delay from the generation and sending of the signal until its receipt back from the access site. The acoustic transmitter and sensors in this embodiment are mounted on the cassette of the therapy machine, such as a hemodialysis machine, and in particular to the flexible membrane of the cassette.

The transmitter may be mounted on the therapy machine and in one embodiment is mounted near the blood return line or output line of cassette 11. Depending on the frequency and amplitude of the acoustic signal needed, different methods are used to induce the signal. A piezo-electric acoustic transducer or actuator may be used. These devices are commercially available from such companies as PI GmbH, Karlsruhe, Germany, and from Ceratec, Inc., Santa Clara, Calif., U.S.A. For larger displacements, an acoustic generator may be made from a moving coil, much like an acoustic speaker. These are available from BEI Kimco Magnetic, Vista, Calif., U.S.A. Other devices may also be used, such as a small motor with a cam or other mechanical device.

The acoustic sensor itself is typically a very small electronic device with a membrane intended to interface with the surface or fluid to be monitored or measured. Thus, the sensor itself will typically be mounted in a small plastic or metallic housing, with an interface or membrane exposed for the measurement surface. When this patent refers to a sensor, it is intended that the term includes both the sensor and the necessary housing. For invasive applications, the acoustic transmitter and sensors may be mounted so that their interfaces are within the fluid lines. The sensors may include threads or quick-disconnects for such mounting. For non-invasive applications, the sensor, or more accurately, the sensor in sensor housing, will then be mounted to the membrane of the cassette very near the outlet of the cassette.

Characteristics of the signal sent by transmitter 18, including its timing, will be controlled and detected by controller 20 of the dialysis machine. In the same manner, the characteristics of the signal detected by sensor 19a will be sent to controller 20. It will be recognized that one or more amplifications, conversions, or transformations will be accomplished by signal processing circuitry in one or more of a multiplexer, the transducer, the sensor, and the controller. For example, transmitter 18 may include an analog to digital converter (ADC) for converting an indication to the controller of the magnitude of the signal that was generated. Sensors 19a, 19b, 19c may include a pre-amplifier and an ADC for amplifying the attenuated signal and for converting the analog signal detected to a digital value to send to controller 20.

Controller 20 is connected to the transducer and sensors via signal and power lines 25. In testing conducted, a piezoresistive Entran EPX-V01-50P transducer, from Entran Devices, Fairfield, N.J., was coupled invasively to the system and used as a transmitter. For measuring signals and coupling through the membrane, or membrane portion, a model 1865 piezoresistive transducer was used, from Honeywell, Inc., Automation and Control Solutions, Freeport, Ill., U.S.A. Piezoresistive sensors are generally good at capturing both static and dynamic acoustic measurements, while piezoelectric sensors are better at dynamic only, and thus may be used as acoustic sensors in a cassette or hemodialysis machine.

Controller 20 may have a digital signal processor 21 for further processing or comparing of signal values. Controller 20 may be a controller of the therapy machine, such as the hemodialysis machine or other therapy machine, or may be a stand-alone controller. The controller also includes a microprocessor 22, memory 23, and a local output device 24. The local output device 24 may be a screen, a printer, or a sound-type alarm. The output will alert the patient or a caregiver to take action, such as ceasing therapy, replacing the disconnected venous access needle, and so forth. The controller may also be programmed to stop blood pumping from the patient to the therapy machine, or from the therapy machine to the patient, or both.

Figure 2:
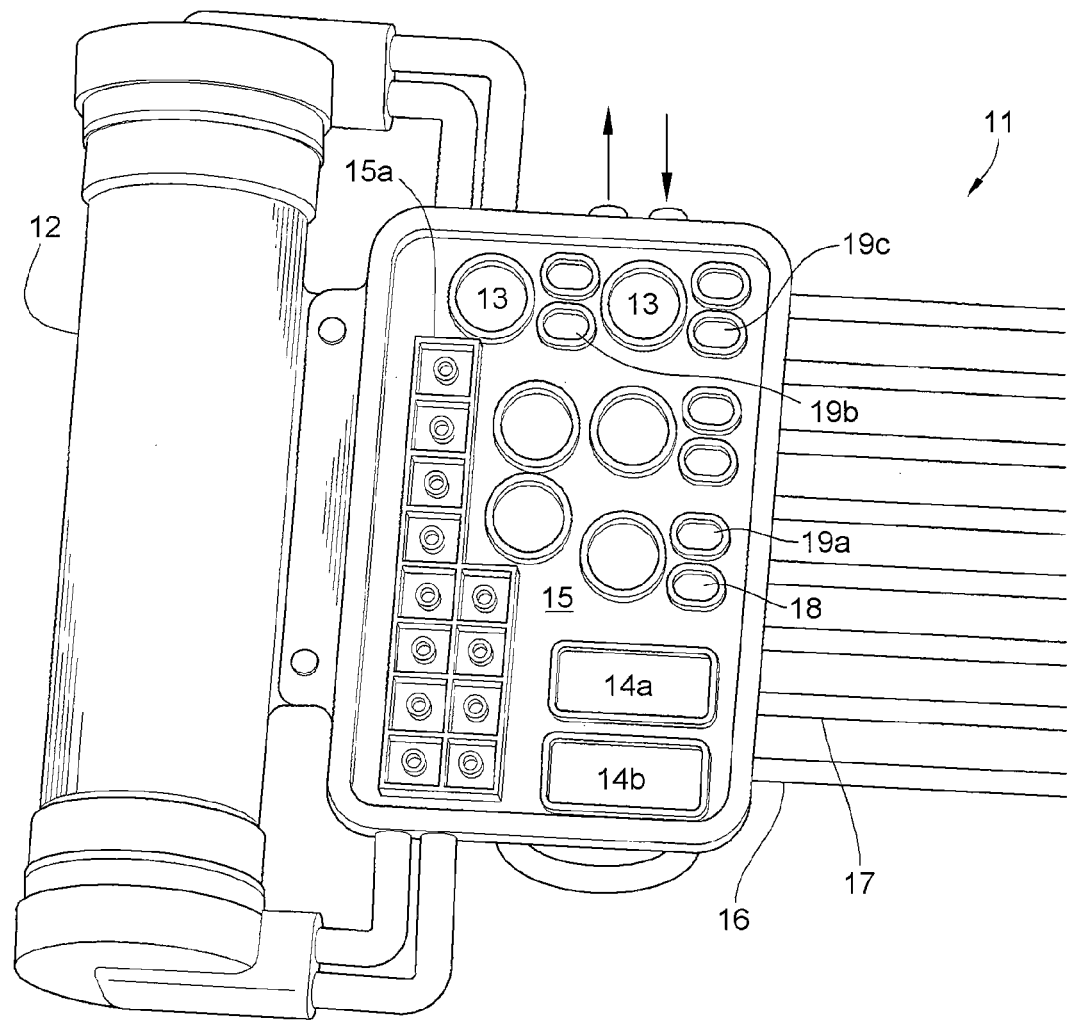
FIG. 2 depicts a plan view of a cassette useful in a hemodialysis machine.

A closer look at cassette 11 is disclosed in FIG. 2, and discloses placement of the transmitter and sensors in this embodiment. Blood from the patient input line 16 and the cassette 11 circulates into dialyzer 12, and is routed back to the patient through venous output line 17. On the side of the cassette depicted, a flexible membrane 15 and valves 15a control the flow of blood and dialysate through the cassette and through the dialyzer. Pumps 13 and drip chambers 14a, 14b are also part of the cassette. The transducer 18 is mounted near the blood return line, as are sensors 19a, 19b. Sensor 19c is located near the blood inlet line. The routing of fluids in the cassette is determined by the positions of valves 15a. The actual positions of the acoustic transmitter and sensors with respect to blood flow are therefore better represented in FIG. 1, while FIG. 2 depicts their positions on a working cassette.

Figure 12:
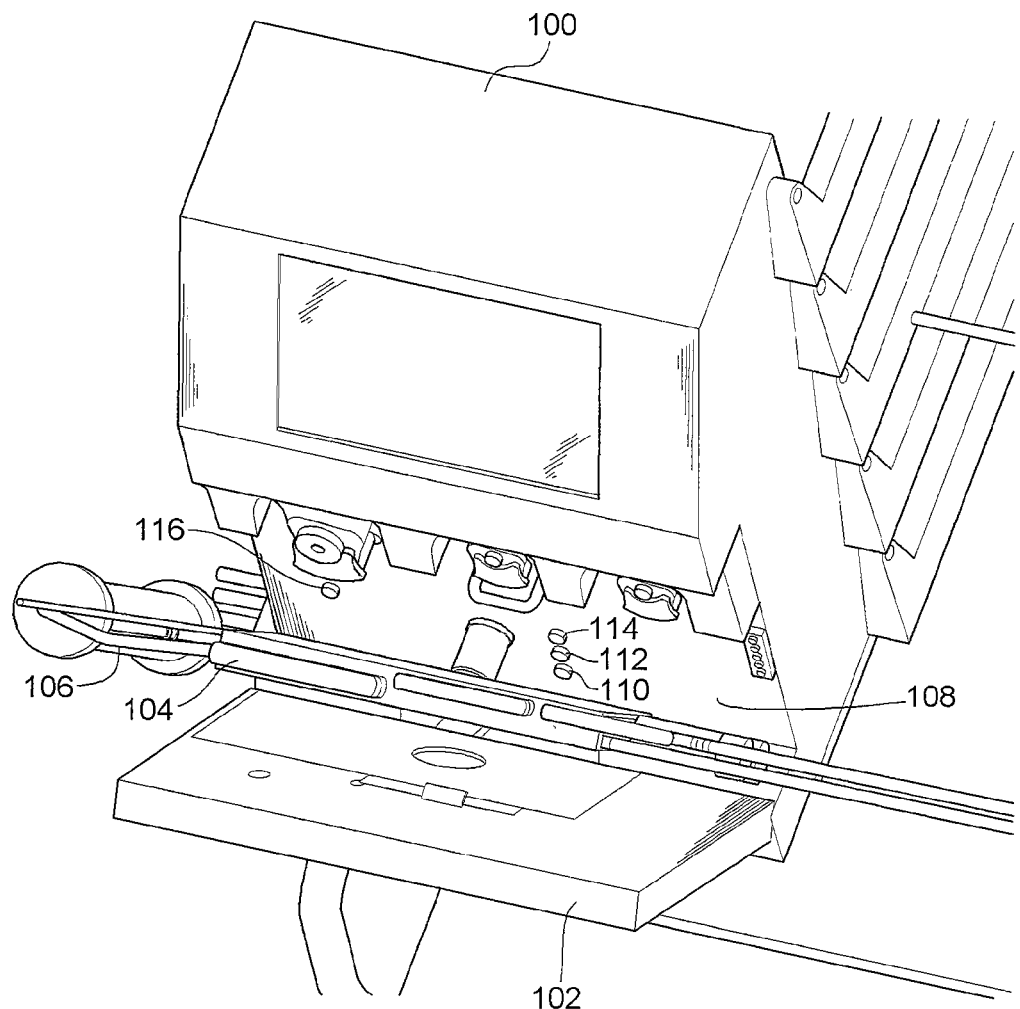
FIG. 12 depicts a hemodialysis machine showing the mounting of the acoustic transmitter and sensors within the machine.

FIG. 12 depicts a hemodialysis machine from a top front perspective. Hemodialysis machine 100 has a door 102 which opens to admit the cassette discussed above. The cassette has dialyzer 106 attached. In this view, the front face 108 of the inside of the hemodialysis machine is visible. The transmitter and sensors are mounted on or behind this face, so that their interfaces protrude and are available for mating with cassette 102, and in particular with the flexible membrane, as also discussed above. In this view, acoustic transmitter 110 is mounted lowest, and acoustic sensors 112, 114, and 116 are also mounted within the panel for interfacing with the cassette.

In some testing, an electrodynamic shaker was used to generate a signal for detection downstream. A signal may also be generated by an acoustic transmitter 18, and the signal will be attenuated as it proceeds from the transducer, through the tubing, through the access site and access needle, and into the patient. The circuitry described above for alerting the patient and the caregiver takes account of this attenuation. In testing with 15 ga and 17 ga needles, access disconnects could easily be detected, as well as leaks of 10% and 50% of the fluid being tested, a water-glycerol mixture to approximate the viscosity of blood, about 3 cP.

In addition to the acoustic sensor 19a adjacent the return line, discussed above, there are alternative or additional locations for sensors for detecting the acoustic signal. For instance, an additional acoustic sensor 19c may be located on the therapy machine, in this instance adjacent the input line. The rationale is to minimize discomfort to the patient by keeping the sensors away from the patient. This also tends to reduce interaction between the patient and the sensor, thus removing user error from the procedure. If the sensor is mounted adjacent the therapy machine blood input line, there are two paths that the signal may take from the acoustic transducer (original signal) to the detecting sensor. The first path is a backward path through the therapy machine. The signal will be highly attenuated in this path. For example, and with respect to FIG. 1, a portion of the signal originating from transducer 18 will travel backwards through blood drip 14a, dialyzer 12, blood drip 14b, and pump 13. The principal attenuation is caused by the pump and the blood drips. The signal will also be attenuated by lengths of tubing or connections between these devices. Thus, the acoustic signal through the therapy machine is expected to be very small.

The signal will also travel in a forward path through the venous access site $V_n$, through the patient P, through the arterial access site A and arterial needle $A_n$, and then to the tubing connecting the arterial access site to the therapy machine. The venous and arterial access sites are typically separated on a patient by several inches, assuming that one arm is used for both arterial and venous access. This method will be difficult to use if the access sites are more widely separated, e.g., an arm and a leg, or two arms.

This method was tried in laboratory testing and was successful. A 12 Hz signal was generated. The signal was measured in the venous sensor 19a as 80 mm Hg. The signal transmitted to the arterial sensor 19c on a hemodialysis machine arterial tubing, as depicted in FIG. 1, was about 2 mm Hg. The signal difference between transmission and receipt was thus 32 dB. Upon disconnection, a further 10 dB loss was detected. The testing could not detect at the arterial input line the portion of the signal that traveled through the hemodialysis machine. In general, with 15-17 ga needles, a reduction of about 30 dB, with a range from about 20-40 dB, occurs between transmission and detection when both the transmitter and the acoustical receiver are on the hemodialysis machine and when the sound path includes both access sites and the patient. After an access disconnect, an additional signal loss is detected.

Figure 3:
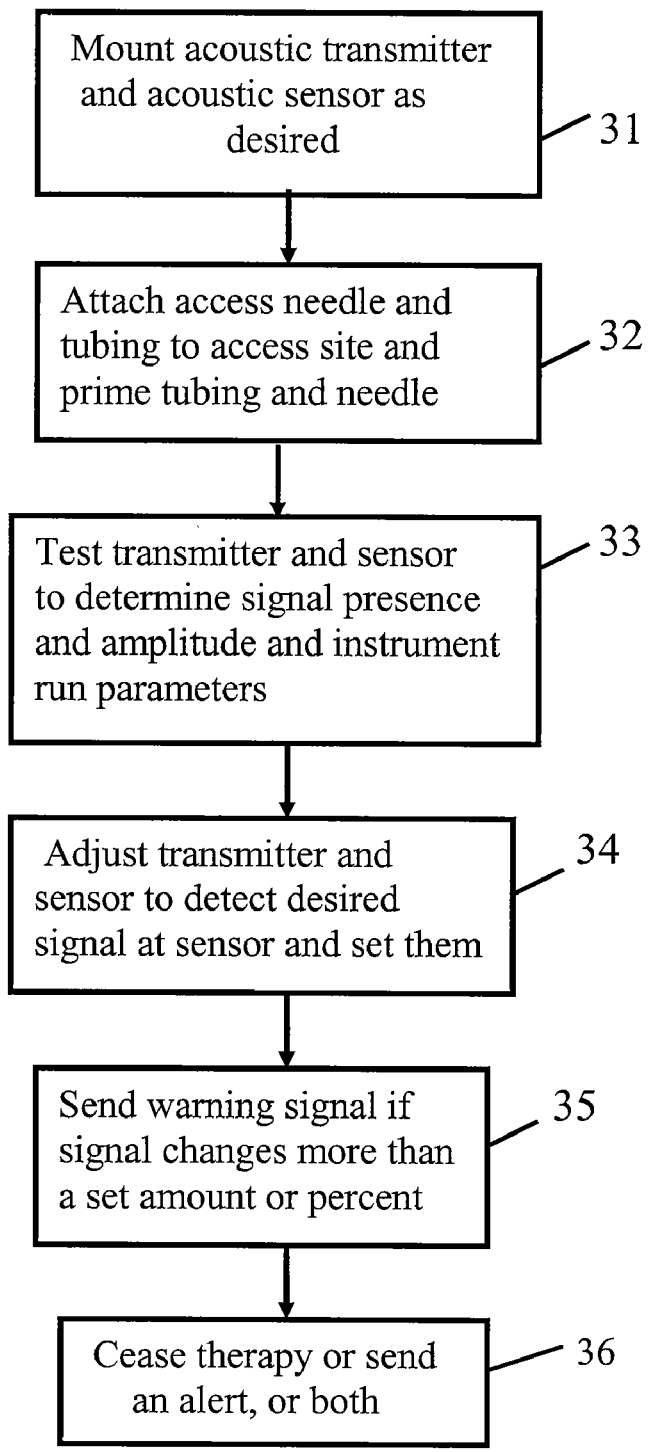
FIG. 3 depicts a method of detecting a venous disconnect using acoustic signals.

Accordingly, each application should account for these differences by running an initial setup, also known as a baseline or initialization. The set-up should insure that the acoustic transmission is detectable by one or more sensors in the particular setting at hand. One method for accomplishing a set up is depicted in FIG. 3. In a first step 31 of the method, the caregiver or patient mounts the acoustic transmitter and acoustic sensor or sensors as desired. In a second step 32, the access needle or needles are then attached to tubing connecting them to the hemodialysis machine, or other therapy machine, and are placed into the patient. The tubing and needle or needles are then primed, that is, filled with blood from the patient. Using the controller from the therapy machine, or other controller, the transmitter and sensor are then tested 33, to insure that the desired signal and amplitude are transmitted and are also received.

It is known that a good deal of attenuation occurs between the transmission and the sensing of the signal, thus the transmitted signal amplitude should ordinarily be at least measureably greater than the detected signal amplitude. The signals should also differ in phase, i.e., the timing of the sending and receipt of the acoustic signal. These differences are sufficient to insure that the signals will indeed change markedly when a disconnect occurs, without having to induce a fault or a disconnect as part of the setup or initialization.

When the signals transmitted and received are as desired, the controller settings and instrument parameter settings are noted and locked or secured in place 34, per the protocol of the clinic or hospital setting. For home settings, the recommended procedures are followed. The therapy, such as hemodialysis, is then begun, and signals are noted. If necessary, the settings and parameters, such as signal amplitude, may be adjusted and again noted and locked or secured in place per the appropriate protocol or procedure followed. Thus, in one embodiment, the baseline may change over time, consistent with the tubing, the sensors, the room temperature, and so on, so that the baseline changes as necessary to insure patient safety while avoiding false alarms. Once therapy has begun, the controller monitors the transmitted and sensed signals and sends a warning signal 35 if either changes more than a previously determined amount, such as a sudden percentage change or sudden dB level change. Monitoring the transmitted level as well as the sensed level is recommended, since a failure or dislodgement of the acoustic transmitter will also result in a change of the signal, and fault analysis or failure resolution will be easier for an operator or the patient if this parameter is tracked as well. Using predetermined criteria based on the signal change or changes, the controller can then cease therapy, send an alert or alarm through a local output device, or take other action to safeguard the patient.

It has been found that continuously sending and receiving acoustic signals, as described above, is not necessary. It is possible to periodically send an acoustic signal and to then periodically detect the signal received. For example, one or more cycles of a 30 Hz sine wave may be sent each second or other time period, such as twice per second. This schedule makes for a repeatable and reliable method for checking the integrity of the access connection. Other periodic checks may be made, for example, from about every one-tenth of a second to about every 1 second, i.e., about 1 to 10 Hz, or from about half-second to about every 2 seconds, i.e., 0.5 to 2 Hz.

In determining whether an access disconnect, a leak, or other event has occurred, baseline readings and the particular application will determine the appropriate signal change needed. As will be seen below, events may cause a change in the signal anywhere in the range from a 100% loss of signal to a 100% gain, and many points in-between that are much more subtle. Each application, each tubing length and arrangement may be different, and these differences may each have an effect on acoustic transmission. Accordingly, the decision points on when the signals are significantly different from the baseline or previous signals so as to suggest a leak or an access disconnect, and thus whether to send a signal or sound an alarm, will best be determined for each site individually. As will be seen in the testing data below, a sudden change in acoustic data is a good indicator of a leak or of needle dislodgement.

Figure 4:
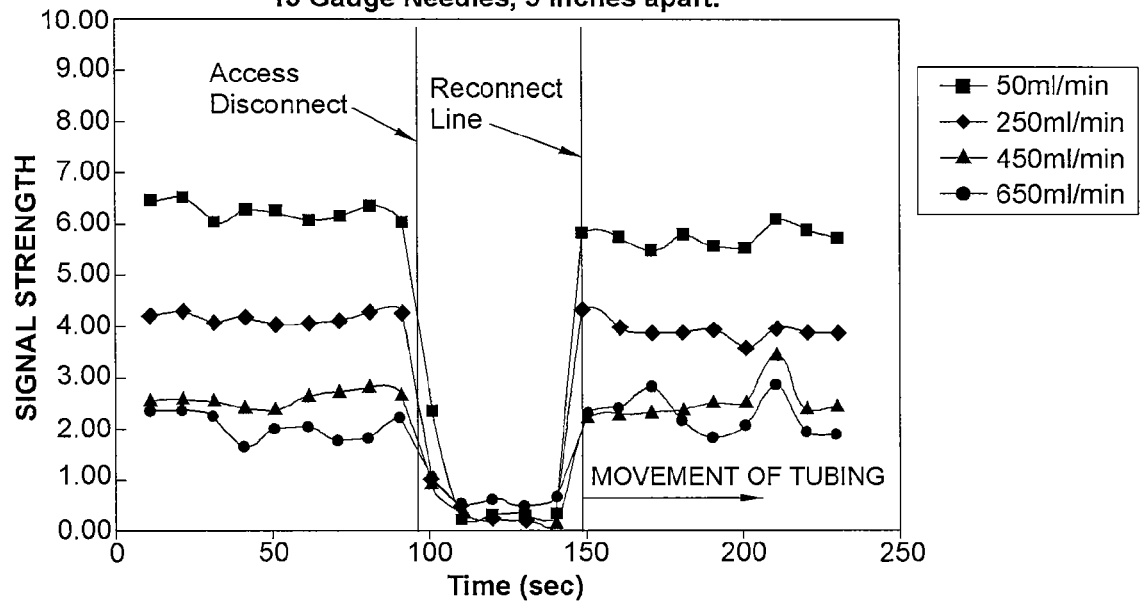
FIG. 4 presents results of acoustic signature testing.

Results of one series of tests are depicted in FIG. 4. This testing was conducted with a simulated hemodialysis treatment, with 15 ga needles on both the arterial and venous access sites. A 12 Hz signal was used, and blood flow was set at 50 ml/min., 250 ml/min., 450 ml/min., and 650 ml/min. A sound pressure level of about 69 mm Hg was generated and transmitted through the blood. The sound pressure level was increasingly attenuated with increasing blood flow levels. As seen in FIG. 4, the acoustic signal was very detectable at the access site. A venous disconnect was readily detected at all four flow rates used. When the needle was re-attached, the signal also returned and the testing continued. The tester also moved the tubing, as indicated in the graph, to determine whether the system was sensitive to patient movement, and determined that the acoustics used were indeed sensitive.

Acoustic Impedance and Reflection Coefficients

In another way to detect a venous access disconnect, acoustic sensor 19a is placed downstream of acoustic transmitter 18, adjacent the blood return line. Downstream, in this context, means in the direction of the flow of blood. The patient's blood here is flowing from the therapy machine back to the patient, along the path from blood drip 14b, through tubing 17 and to the access site $V_n$. Thus, an acoustic signal is generated by transducer 18 and travels with the blood to the access site. Acoustic sensor 19a is placed between the transducer 18 and the access site, with both transducer 18 and sensor 19a on the therapy machine. In the same vein, upstream means opposite the flow of the blood. In the example above, if the acoustic sensor 19a is downstream of acoustic transmitter 18, as shown in FIG. 1, both the transmitter 18 and sensor 19a are upstream from venous access site V, that is, the blood flows to access site V only after the blood has passed transmitter 18 and sensor 19a. In general, movement in the cycle depicted in FIG. 1 in a clockwise direction is upstream movement, while movement in a counter-clockwise direction is downstream. If an additional acoustic sensor 19b is placed adjacent sensor 19a, the acoustic impedance and reflection coefficient methods may be used to monitor signals continuously.

In one method, a signal is generated by the transmitter, and is picked up by the sensor. Of course, the signal that is received is not only the signal directly from the transducer, but also signals reflected back from the needle, the access site, and so forth. If the acoustic signal travels in two media, a first medium, such as water or blood, and a second medium, such as water or blood mixed with air, there will be a difference in the transmission rates of sound through the media. Thus, if a leak or if dislodgement occurs, the normally-occurring reflection caused by the interface, will change. The reflection coefficient is defined as the reflected acoustic pressure divided by the incident acoustic pressure, Pr/Pi. The impedance ratio is then defined as the ratio of 1+the reflection coefficient divided by 1−the reflection coefficient. It is recognized that the reflection coefficient is a complex value, allowing calculation of both magnitude of the reflection coefficient and change of phase.

Figure 5:
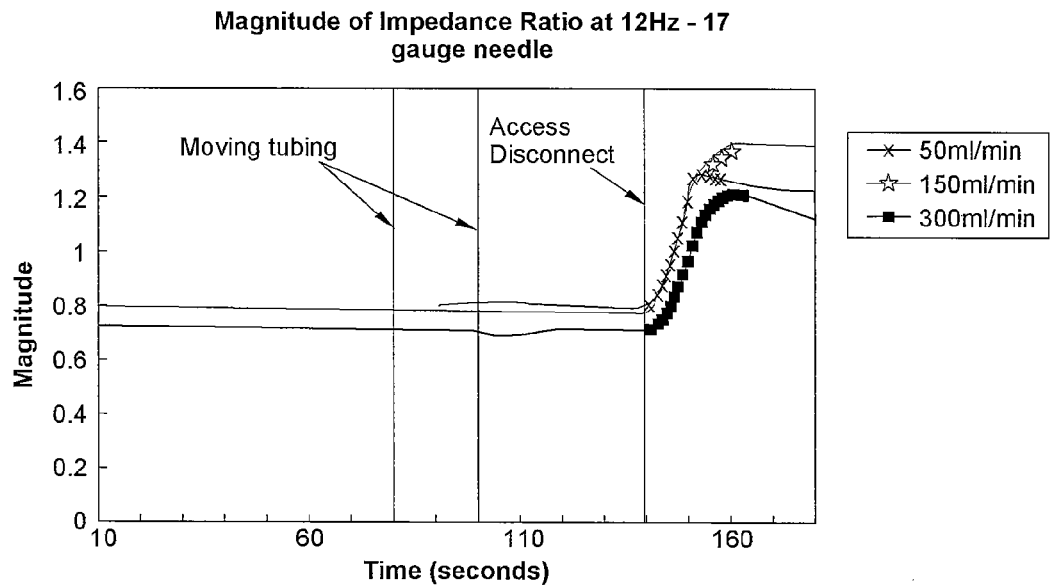
FIGS. 5-6 depict results of testing using an impedance ratio as a detecting parameter.
Figure 6:
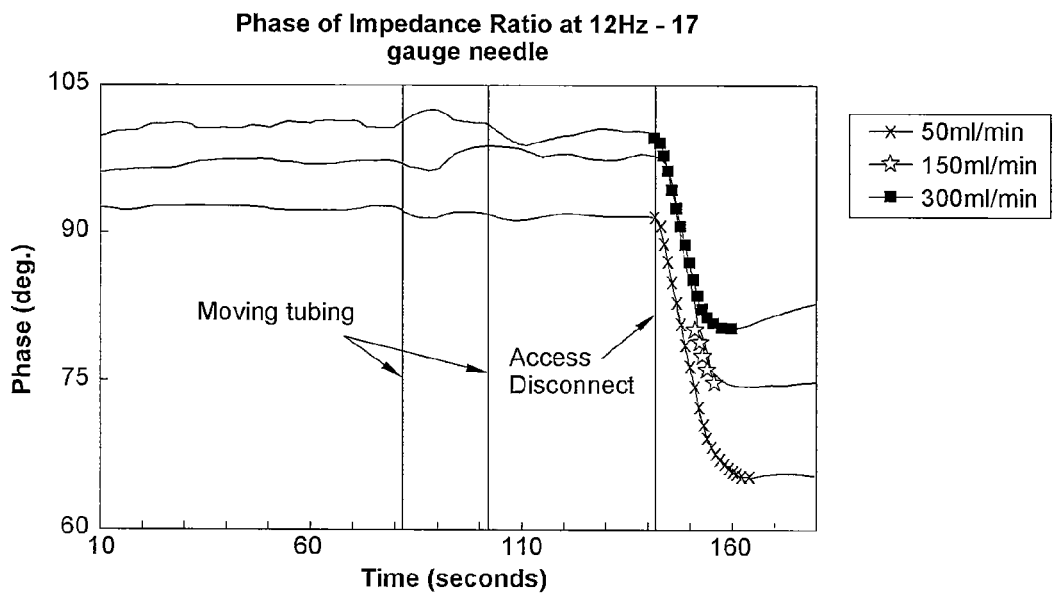

The impedance ratio and the reflection coefficient are both useful in detecting access disconnects and leaks. In experimental work with the impedance ratio, it was discovered that not only is the magnitude of the impedance ratio useful, but also the differences in phase of the reflected wave, that is, the phase of the impedance ratio, and its timing shift upon the occurrence of a leak or a discontinuity. FIGS. 5-6 depict results of testing using 2.7 cP simulated blood, 17 ga needles, and a 12 Hz acoustic signal. Flow rates of 50 ml/min., 150 ml/min., and 300 ml/min. were used. In FIG. 5, the magnitude of the impedance ratio was quiescent at about 0.8 (arbitrary units) at all three flow rates. Rearranging the tubing from the blood pump to the access site, as depicted on the graphs, changes the impedance ratio a little, after which the ratio resumes a relatively continuous value.

When the needle is disconnected from the access site, a great change is observed, an increase in the magnitude of the impedance ratio, which suggests greater impedance, additional reflected signals, and a higher impedance ratio. As also seen in FIG. 6, the phase of the impedance ratio also changes. The phase is simply the difference in timing between the incident wave and the reflected wave. As seen in FIG. 6, the quiescent phase is different at each flow rate, and the phase difference increases with increasing flow rate, suggesting a greater phase difference as the flow rate increases. There is little effect from moving or adjusting the tubing, but a very noticeable effect when a discontinuity occurs. This testing was also conducted with 17 ga needles and a 12 Hz acoustic signal. Very similar results were also seen with 15 ga needles.

Figure 7:
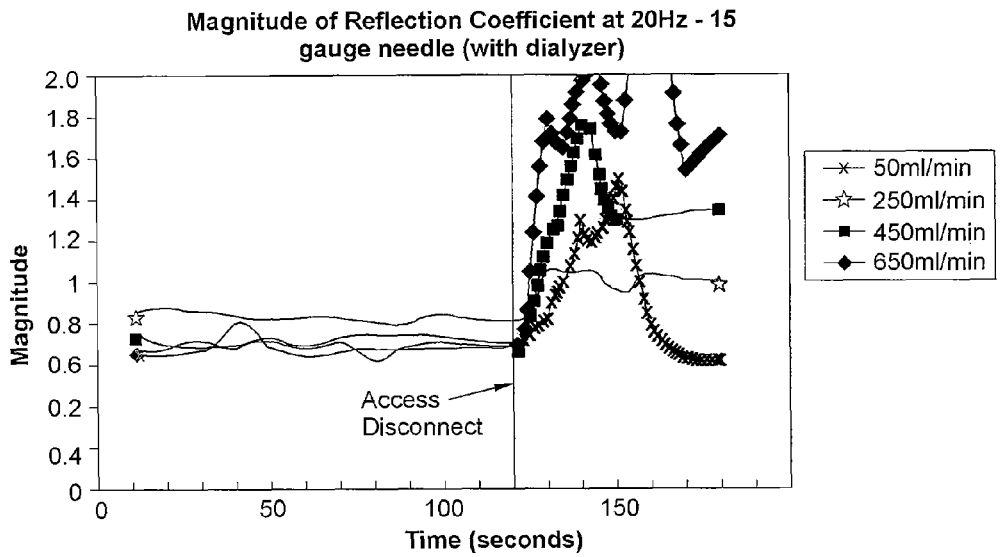
FIGS. 7-8 depict results of testing using a reflection coefficient as a detecting parameter.
Figure 8:
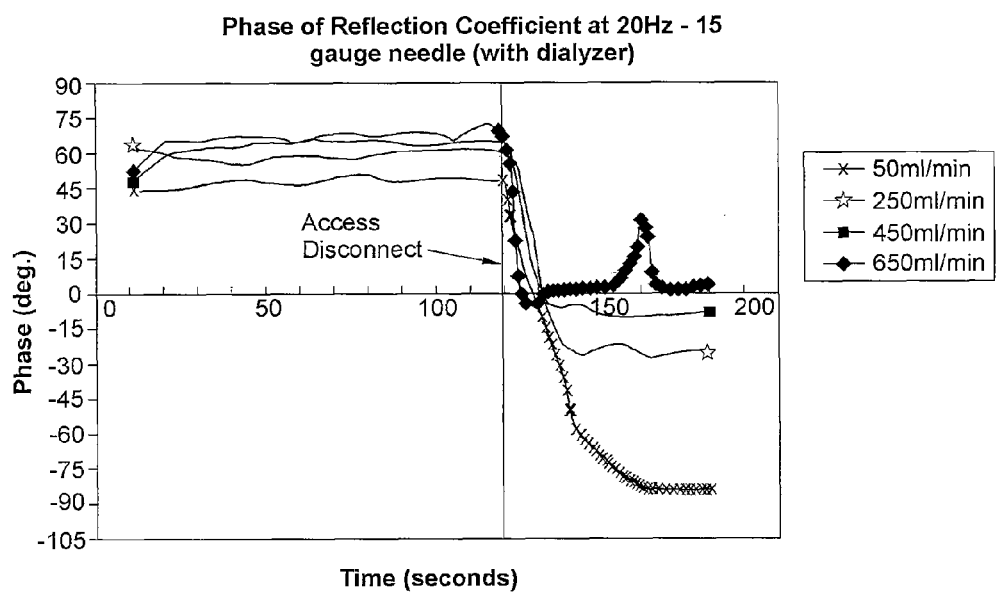

Additional testing was also conducted to determine whether the reflection coefficient would be a suitable parameter for detecting access disconnection or leaks. In FIGS. 7-8, testing was conducted using the same simulated blood, but with larger 15 ga needles and using a 20 Hz acoustic signal. The reflection coefficients were calculated as discussed above and were plotted, as seen in FIG. 7, against time at four flow rates, 50 ml/min., 250 ml/min., 450 ml/min., and 650 ml/min. As seen in FIG. 7, the magnitude of the reflection coefficient is relatively quiescent at all four flow rates, until an access disconnect was induced. The effect on the magnitude of the reflection coefficient is immediate, within seconds, and dramatic, in that a very large change is observed. FIG. 8 depicts the changes from the same access disconnect while recording the phase of the reflection coefficient. The effect there is also immediate and dramatic, as the phase, or timing, of the reflected waves changes dramatically.

Leakage detection

Figure 9:
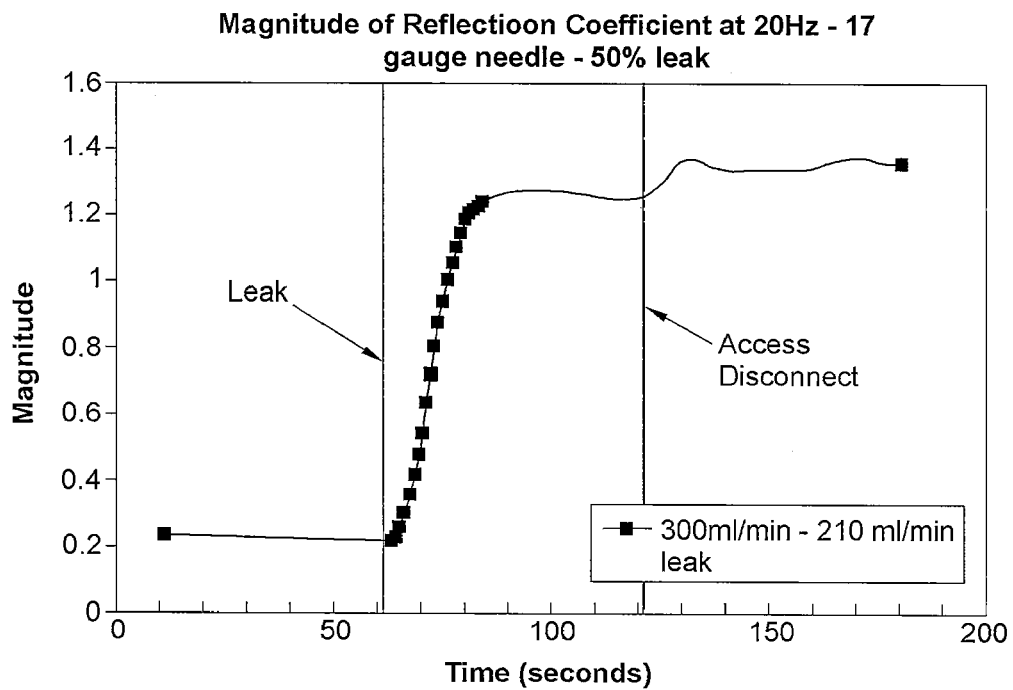
FIGS. 9-10 depict testing results using impedance ratio to detect access site leaks.
Figure 10:
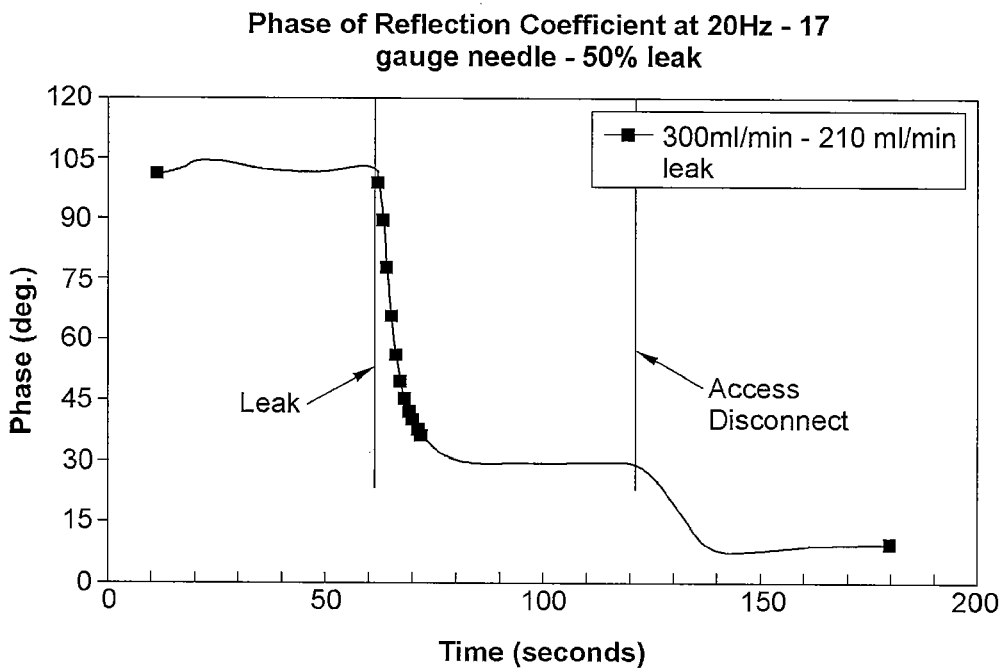

Impedance ratios and reflection coefficients are also useful for detecting leaks in the access site. A leak will at least cause loss of blood or fluid and may also cause infiltration of air. Thus, the transmission medium will change, and in theory, should show a difference in acoustic impedance, impedance ratio and reflection coefficients. FIGS. 9-10 depict the use of the impedance ratios and reflection coefficients mentioned above to detect not only access disconnects but also leaks from the access site. In these tests, an orifice was drilled in the proximal end of a 17 ga needle used in the testing. The leak was calculated at about half the flow rate of blood through the needle. As seen in FIG. 9, the leak is readily detectable using the magnitude of the impedance ratio. After an initial signal change, the acoustic signal adjusts to a new and distinct level as the leak continues. When the needle is disconnected, another very distinct change takes place, as discussed above. FIG. 10 depicts the phase of the impedance ratio in this series of tests. The phase also shows dramatic differences both when a leak occurs and when the access needle is disconnected. This testing was conducted with a 20 Hz acoustic signal.

Heart Beat Acoustic Detection

Figure 11:
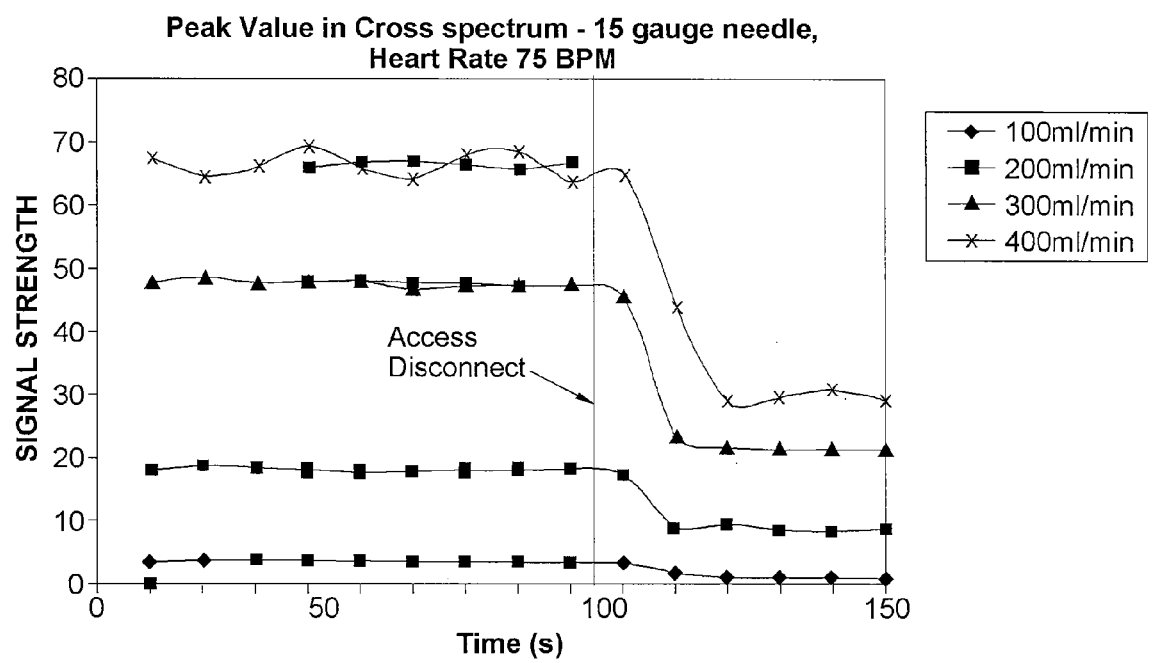
FIG. 11 depicts a test result using a patient's heartbeat to detect a disconnect at the venous access site.

The heart beat of the patient can also be used to transmit an acoustic signal useful for detecting access disconnections. With most heart beats ranging from 50 to 85 beats per minute, a rate of about 1-2 Hz is the expected value of the signal. In this testing, a simulated heart beat of about 75 beats per minutes was used, with a 15 ga needle in the access site. Blood flow rates from about 100 to 400 ml/min. were used, and as seen in FIG. 11, access disconnect was readily detectable. The acoustic sensor was placed on the venous side. The sensor may be placed at any convenient location on the hemodialysis or other therapy machine, such as just downstream of the drip chamber or, if there is a return pump, between the return pump and the access site.

The signal processing circuitry used for detection of the heart beat may also be used for signal detection and processing of the other methods discussed above. Among many other known methods, four quantization methods are pertinent. The method known as peak detection searches for and identifies the peak value of the magnitude of the venous acoustic signals within a prescribed frequency band. The program may be instructed to search for the largest peak within a particular period of time. The controller may be "tuned" by segmenting into larger or smaller periods of time, usually defined in milliseconds. For example, if a 30 Hz acoustic signal is used, searching for the largest peak in every 30 or 40 msec band may be appropriate. If a heartbeat is used, about 50 to 85 beats per minute, about 1-2 Hz, a much larger band would be better suited to this technique.

The technique of power in band measures the spectral power of venous acoustic events. Using this technique, the spectral power within a prescribed frequency band is calculated and recorded, and used to characterize the acoustic signature. A cross spectrum or cross spectral technique, also known as a cross correlation technique, calculates the peak value of the magnitude of the cross spectra of the venous and arterial acoustic events. The values are calculated and recorded. Finally, an auto spectrum technique calculates the peak value of the magnitude of the auto power spectrum for venous acoustic activity. All four techniques were tested and worked well in using the patient's heartbeat for detecting venous access disconnect, but the cross spectrum and auto spectrum methods worked better. In addition, these processing techniques may also be used to process acoustic signatures. Software packages with these techniques may be purchased commercially from many companies. Examples are the AutoDAQ2 software from InterAC, L'Union, France and the LabVIEW software from National Instruments, Santa Clara, Calif., U.S.A.

It will be recognized that the transmission and detection of an acoustic signal through several media, such as access tubing, an access needle, a patient, and so forth, is not completely a straightforward task. The many variables that will attend each situation include the length or lengths of tubing, the mounting of the transducer and sensor or sensors, the length and gauge of the needle or needles, and the separation between the arterial and venous needle. This suggests that each application of acoustic technology for detecting access disconnect will be at least slightly different.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. An access disconnect detector for use with an extracorporeal circuit, the detector comprising:
    an acoustic transmitter for producing an acoustic signal and configured for mounting on a venous side of the extracorporeal circuit;
    an acoustic sensor for sensing a signal from the acoustic transmitter, the acoustic sensor mounted on the venous side of the extracorporeal circuit; and
    a controller configured for (i) sensing a signal from the acoustic transmitter and the acoustic sensor and for sending an alert upon a change in the signal detected from the acoustic transmitter or the acoustic sensor, (ii) calculating a baseline acoustic reflection coefficient for the signal, wherein the reflection coefficient includes a reflected acoustic pressure divided by an incident acoustic pressure, and (iii) calculating a change from the baseline coefficient to determine when a leak or a disconnect has occurred, wherein the controller is in communication with or is part of a therapy machine for receiving blood and returning blood to the venous access site.

2. The access disconnect detector of claim 1, wherein the acoustic transmitter is configured for sending signals from about 5 Hz to about 30 Hz.

3. The access disconnect detector of claim 1, wherein at least one of the transmitter and the sensor are mounted on a cassette for a hemodialysis machine, and further comprising the cassette and the dialysis machine.

4. The access disconnect detector of claim 1, further comprising a hemodialysis machine mounting the transmitter, sensor and controller.

5. The access disconnect detector of claim 1, wherein further comprising a second acoustic sensor mounted adjacent the acoustic sensor, wherein the acoustic sensor and the second acoustic sensor are configured for continuously sensing the signal.

6. The access disconnect detector of claim 1, wherein the controller further comprises a computer program for a signal processing program consisting of one or more programs selected from the group consisting of peak detection, power in band, cross spectrum, and auto spectrum.

7. The access disconnect detector of claim 1, wherein the controller is further configured to stop pumping from the therapy machine to a patient or from the patient to the therapy machine when the leak or disconnect has occurred.

8. The access disconnect detector of claim 1, wherein at least one of the acoustic transmitter and the acoustic sensor are mounted on a flexible membrane of a cassette for a therapy machine, and further comprising the cassette.

9. The access disconnect detector of claim 1, wherein the acoustic transmitter is selected from the group consisting of a piezoelectric actuator and a speaker with a moving coil.

10. A system for use with an extracorporeal circuit and an access disconnect detector, the system comprising:
    a therapy machine;
    a pumping cassette operated by the therapy machine;
    an acoustic transmitter mounted on the therapy machine adjacent the cassette of the therapy machine on a venous side of the extracorporeal circuit, the transmitter configured for pulsing a flexible membrane of the cassette to produce an acoustic signal;
    at least one acoustic sensor for sensing a signal from the acoustic transmitter, the acoustic sensor mounted on the venous side of the extracorporeal circuit; and
    a controller configured for (i) sensing a signal from the acoustic transmitter and the acoustic sensor and for sending an alert upon a change in the signal from the acoustic transmitter or the acoustic sensor, (ii) calculating a baseline acoustic reflection coefficient for the signal, wherein the reflection coefficient includes a reflected acoustic pressure divided by an incident acoustic pressure, and (iii) calculating a change from the baseline coefficient to determine when a leak or a disconnect has occurred, wherein the controller is in communication with or is part of a therapy machine for receiving blood and returning blood to a patient.

11. The system of claim 10, wherein the acoustic transmitter is a piezoresistive transducer.

12. The system of claim 10, wherein the acoustic transmitter comprises a sine-wave or square-wave generator.

13. The system of claim 10, wherein the acoustic transmitter is mounted downstream of a drip chamber of the therapy machine.

14. A method for detecting an access disconnection, the method comprising:
    sending an acoustic signal in a venous line of an extracorporeal circuit, the venous line communicating fluidly with a venous access device;
    detecting the acoustic signal via an acoustic sensor in the venous line of the extracorporeal circuit;
    comparing the detected acoustic signal with baseline detected acoustic signals;
    deciding whether the detected acoustic signal is significantly different from the baseline detected acoustic signals;
    sending an alert if the detected acoustic signal is significantly different from the baseline acoustic signals;
    calculating a baseline acoustic reflection coefficient for the detected acoustic signal, wherein the reflection coefficient includes a reflected acoustic pressure divided by an incident acoustic pressure; and
    determining when an access leak or disconnect has occurred when a change from the baseline acoustic reflection coefficient occurs.

15. The method of claim 14, wherein the acoustic signal is detected between the point of origin of the acoustic signal and: i. the venous access device; or, ii. a point on a therapy machine.

16. The method of claim 14, wherein the detecting of the acoustic signal is via a controller in communication with or part of a therapy machine for receiving blood and returning blood to the venous access site, and comprising:
    programming the controller to stop blood pumping from the therapy machine to a patient or from the patient to the therapy machine.

17. The method of claim 14, wherein the signal that is sent is from about 5 Hz to about 50 Hz.

* * * * *

UNITED STATES PATENT AND TRADEMARK OFFICE
CERTIFICATE OF CORRECTION

PATENT NO. : 8,197,431 B2
APPLICATION NO. : 11/859561
DATED : June 12, 2012
INVENTOR(S) : Bennison Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 656 days.

Signed and Sealed this
Seventeenth Day of March, 2020

Andrei Iancu
*Director of the United States Patent and Trademark Office*